United States Patent [19]

Kipp

[11] Patent Number: 4,746,295

[45] Date of Patent: May 24, 1988

[54] CONNECTING ELEMENT FOR DETACHABLY CONNECTING A PARTIAL DENTURE TO A REMAINING SET OF TEETH

[76] Inventor: Manfred Kipp, Rustringer Str. 1a, 2945 Sande 1, Fed. Rep. of Germany

[21] Appl. No.: 893,096

[22] Filed: Aug. 4, 1986

[30] Foreign Application Priority Data

Aug. 6, 1985 [DE] Fed. Rep. of Germany ....... 3528144
Apr. 9, 1986 [DE] Fed. Rep. of Germany ....... 3611901

[51] Int. Cl.$^4$ ................................................. A61C 13/12
[52] U.S. Cl. ...................................... 433/182; 433/181; 433/183
[58] Field of Search ................. 433/182, 181, 180, 183

[56] References Cited

U.S. PATENT DOCUMENTS

| | | | |
|---|---|---|---|
| 1,753,644 | 4/1930 | Burden | 433/181 |
| 1,941,096 | 12/1933 | Lasky | 433/182 |
| 2,127,285 | 8/1938 | Brecht | 433/182 |
| 3,091,032 | 5/1963 | Hirshhorn | 433/182 |
| 3,117,377 | 1/1964 | Poveromo | 433/182 |
| 4,196,516 | 4/1980 | Poveromo | 433/182 |
| 4,380,436 | 4/1983 | Kipp | 433/182 |

Primary Examiner—John J. Wilson
Attorney, Agent, or Firm—Collard, Roe & Galgano

[57] ABSTRACT

A connecting element is provided for detachably connecting a partial denture with the remaining set of teeth. The element is a joint whose axle extends transversely to the row of teeth and is formed by a bolt displaceably supported in the joint. The joint has two ring-shaped bolt-receiving devices, a first bolt-receiving device is connected with the partial denture and a second bolt-receiving device is connected with the remaining set of teeth and the bolt-receiving devices are connected with each other by the bolt.

7 Claims, 5 Drawing Sheets

CONNECTING ELEMENT FOR DETACHABLY CONNECTING A PARTIAL DENTURE TO A REMAINING SET OF TEETH

The present invention relates to a connecting element for detachably connecting a partial denture to a remaining set of teeth.

With known connecting elements of this type, the partial denture is joined with the remaining set of teeth by means of finished locking or bracing parts. For example, it is known to use pivoting and rotating bars or braces for this purpose. In addition, the use of sliding buttons or press-buttons for connecting the partial denture with the remaining set of teeth is well known.

The pressure of the act of chewing subjects the teeth of the partial denture to tensile stress which is transmitted to the remaining teeth by the known rigid connecting elements. This results in great stress and damage to the remaining teeth. Furthermore, these stresses subject the connecting elements to wear as well, leading to loss of proper fit, so that the connecting elements no longer offer firm support for the partial denture and must be replaced by new connecting elements at relatively high cost.

It is, therefore, the object of the present invention to provide a connecting element of the type specified above which improves the distribution of pressure resulting from chewing.

The above object is accomplished in accordance with the present invention by providing a connecting element in the form of a joint having its axis extending transversely to the row of teeth. The partial denture and the remaining set of teeth are connected with each other in such a way that they are movable with respect to each other by means of this joint. This arrangement has the advantage that only a minor portion of the chewing pressure which stresses the partial denture is transmitted to the remaining teeth by means of the connecting element. The major portion of the chewing pressure is absorbed mainly by a saddle part. The saddle part normally has the partial denture arranged thereon and rests on the crest of the maxilla so that the chewing pressure absorbed by the saddle part is transmitted to the crest of the maxilla across a relatively large area. In this way, the remaining set of teeth and the connecting element itself are stressed to a lesser degree and subjected to less wear.

Preferably, the joint is designed to be detachable by providing the axle of the joint in the form of a bolt which is displaceably supported in the joint. The joint has two bolt-receiving devices preferably in the shape of rings, of which a first bolt-receiving device can be connected with the partial denture and a second bolt-receiving device can be connected with the remaining set of teeth, the bolt-receiving devices being connected with each other by the bolt. The bolt can be pulled from at least one of the bolt-receiving devices, so that the two bolt-receiving devices and thus also the remaining set of teeth and the partial denture can be separated from each other.

In a manner known per se, the second bolt-receiving device may be connected with a crown, which may serve for crowning at least the tooth of the remaining set of teeth that is disposed adjacent to the partial denture, which permits connecting the second bolt-receiving device in an advantageous manner solidly with the remaining set of teeth.

In a preferred embodiment of the joint according to the present invention, the bolt is displaceably or slideably supported in the first bolt-receiving device, and the bolt has two stops limiting its path of displacement in both directions. Advantageously, the bolt may be displaced in the first bolt-receiving device to an extent such that it releases the second bolt-receiving device, so that the two bolt-receiving devices may be detached from each other. The bolt is retained on the first bolt-receiving device by the stops, so that it cannot completely slide out and possibly get lost. Preferably, the first bolt-receiving device, in which the bolt is supported, is arranged adjacent to the inner sides of the teeth, so that the bolt may be advantageously pushed into the second bolt-receiving device with the help of the tongue.

Preferably, the partial denture grips over the connected bolt-receiving devices so that the partial denture is joined with the remaining set of teeth without any gaps. For example, the first bolt-receiving device may be integrated in the walls of a hollow artificial tooth, and the second bolt-receiving device, which is connected with the remaining set of teeth, may be pushed into the hollow space of the artificial tooth through a lateral slot. Preferably, when the bolt is in its inserted or pushed-in position, its face side directed at the mouth cavity is disposed flush with the wall of the hollow artificial tooth, so that the bolt may be pushed out of the artificial tooth with a mandrel or the like through an access opening arranged in the wall of the artificial tooth, this opening conforming to the bolt-receiving devices.

According to another feature of the invention, the first bolt-receiving device is part of a forked head which is formed by the first bolt-receiving device and a tongue arranged approximately parallel thereto. The tongue has a through-extending bore corresponding with the opening of the annular first bolt-receiving device, with the diameter of the bore conforming to the diameter of the bolt. The minimum spacing between the first bolt-receiving device and the tongue approximately conforms to the width of the second bolt-receiving device. When in its inserted or pushed-in position, the bolt is supported on its end sides both in the opening of the first bolt-receiving device and in the through-extending bore of the tongue, which means the bolt, when inserted in the joint, is guided in three guides. The tongue, like the first bolt-receiving device, may be integrated in the wall of an artificial tooth. The second bolt-receiving device can be inserted between the first bolt-receiving device and the tongue. When the bolt is in the inserted position, the opening of the second bolt-receiving device is penetrated by the bolt, which locks the second bolt-receiving device in the fork. When the bolt is in its pulled-out position, the second bolt-receiving device may be pulled from the fork. Preferably, the spacing between the first bolt-receiving device and the tongue exactly conforms to the width of the second bolt-receiving device, so that the latter is fixed in the fork without play or clearance.

In a possible embodiment, the first stop limiting the path of displacement of the bolt in the pushed-in direction is a head arranged at the end of the bolt which may be embedded in a recess or deepening arranged in the first bolt-receiving device so that when the bolt is in its inserted position, the head is flush with the wall of the first bolt-receiving device. The advantage of this arrangement is that no sharp edges project from the first bolt-receiving device that may lead to injury within the cavity of the mouth.

The second stop limiting the path of displacement of the bolt in the first bolt-receiving device may advantageously be a snap ring arranged on the bolt for preventing the bolt from being pulled from the first bolt-receiving device. However, this snap ring may be removed from the bolt when the removal of the bolt from the first bolt-receiving device is desired, for example for cleaning purposes or for changing the bolt. Preferably, the bolt has an annular groove in which the snap ring is mounted. On its face side facing the first bolt-receiving device, the second bolt-receiving device preferably has a recess for receiving the snap ring, so that the snap ring may be mounted in this recess when the bolt is in its inserted position. The path of displacement or distance of displacement of the bolt is advantageously extended by the amount of this recess. Furthermore, the snap ring advantageously assumes the function of a sealing element, which makes it more difficult for food to penetrate the bolt-receiving device, which penetration may impair the function of the joint.

According to another feature of the invention, the bolt has a groove extending parallel to its longitudinal central axis, the groove being radially engaged by a projection arranged on the first bolt-receiving device. This projection engaging the groove of the bolt advantageously prevents the bolt from rotating about its longitudinal central axis. Since the first bolt-receiving device preferably is integrated in the wall of an artificial tooth and the head of the bolt, which is normally present, must be embedded flush in this wall, the outwardly pointing face side of the head of the bolt must have a surface design such that it is continuous with the surface of the wall of the tooth. This means that the surface of this face side of the bolt is not necessarily axially symmetrical with the longitudinal center axis of the bolt. If the bolt were supported in the first bolt-receiving device in such a way that it would be rotatable about its longitudinal central axis, the surface of its face side would not be flush with the surface of the teeth in most positions of rotation. The result of this is that parts of the bolt's face side edge could project from the surface of the teeth and lead to injury within the mouth cavity.

According to a preferred embodiment of the connecting element of the invention, a yielding arresting or locking element projecting into the path of displacement of the bolt is arranged on the first bolt-receiving device. The arresting element is lockable in two receiving elements arranged in the bolt, whereby the wall zones of the receiving elements that are closest to the face sides of the bolt are formed by the stops limiting the path of displacement of the bolt. Advantageously, a thickened head of the bolt and a snap ring as stop means may be dispensed with because the bolt can be displaced only until the arresting or locking element engages one of the two receiving elements, whereby the bolt is fixed in each of its final positions by the engagement of the arresting or locking element.

Preferably, the arresting or locking element is a flexible pin, for example made out of wire, which, in a secant-like manner, is clamped at both ends in the wall of the first bolt-receiving device. The elements for receiving this pin are preferably grooves which are arranged in the bolt transversely to the longitudinal axis of the bolt. The flanks of the grooves that are disposed closest to the face sides of the bolt extend approximately transversely to the longitudinal central axis of the bolt so that they may function as stops. The flanks of the grooves opposing these stops extend in a flatter way, so that when the bolt is displaced, the pin may be released again in said direction. When released, the pin, which is clamped at both ends, is bent or curved in its central zone in the direction of the wall of the first bolt-receiving device. So as to provide the arched pin with space for yielding, the wall of the first bolt-receiving device is preferably provided with two holes corresponding with each other, and the ends of the pin are inserted in these holes. Furthermore, an elongated or oblong recess, which, in a preferred embodiment, is a slot, is arranged in the wall of the first bolt-receiving device within the zone between the holes for receiving the flexible pin, the slot extending parallel to the pin. Preferably, the area of the bolt supporting the pin which is defined or limited by the grooves, is bevelled to form an approximately hip roof-shaped profile, with the ridge line of the profile slidingly resting against or on the pin, the ridge line extending parallel to the longitudinal axis of the bolt. The hip roof-shaped profile provides for displacement and bending or arching of the pin in the direction of the wall of the first bolt-receiving device, and the bevelled gable surfaces of the hip roof-like profile, which surfaces are flanks of the grooves, permit the pin to be released from the grooves.

Irrespective of the specific design of the arresting element and of the elements for receiving the arresting element, the latter provides not only for a limitation of the path of displacement of the bolt but also for a rotation-resistant arrangement of the bolt, so that the bolt cannot be rotated around its longitudinal central axis. Advantageously, no groove is required in the bolt for radially engaging a projection.

Preferably, the arresting element may be designed in such a way that, advantageously, the bolt can be completely removed from the bolt-receiving devices. For example, the pin may be pulled from the wall of the first bolt-receiving device.

In a preferred embodiment of the connecting element of the invention, the second bolt-receiving device has an outwardly protruding projection. This projection comes to rest on a connecting element connecting the first bolt-receiving device and the tongue with the fork when the second bolt-receiving device is inserted in the head of the fork and when the bolt-receiving devices are in a predetermined rotary position relative to each other. This projection limits the possible angle of rotation of the two bolt-receiving devices relative to each other. When the projection rests against the connecting element at the predetermined position of rotation, the chewing pressure which stresses the teeth is additionally transmitted to the second bolt-receiving device by way of the projection, so that the chewing pressure is distributed in a more favorable manner.

Since the path of displacement of the bolt is restricted, one end of the bolt continues to project into the second bolt-receiving device even when the bolt is extended. The second bolt-receiving device, in a preferred embodiment, has a slot in its wall which is open on one side towards the face side of the second bolt-receiving device that faces the first bolt-receiving device. The minimum width of this slot is such that it conforms to the thickness of the end of the bolt projecting into the second bolt-receiving device, so that in spite of the end of the bolt still projecting into the second bolt-receiving device, the second bolt-receiving device may be removed from the first bolt-receiving device by guiding the projecting end of the bolt from the second bolt-receiving device through the slot of the second bolt-receiving device. Preferably, the end projecting into the second bolt-receiving device may be slimmer than the rest of the bolt, for example by flattening the projecting end of the bolt.

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

Figure 1:
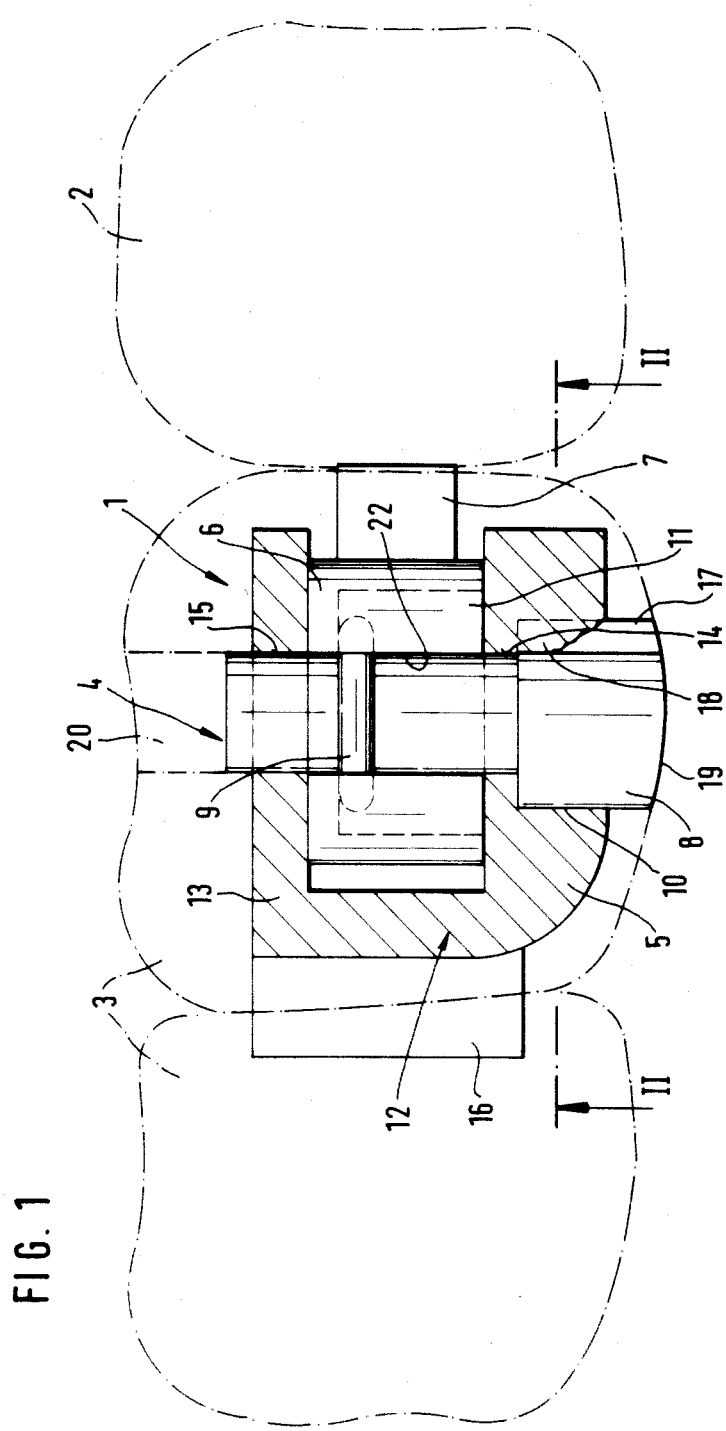
FIG. 1 is a partial cross-sectional top view of a first embodiment of a connecting element according to the present invention.

Now turning to the drawings, there is shown in FIG. 1 a partial cross-sectional top view of the connecting element according to the invention. The connecting element is designed as a joint 1 for connecting a partial denture, of which the two artificial teeth 3 are indicated in phantom, with a remaining set of teeth, of which FIG. 1 shows the contours of a tooth 2 in phantom.

Joint 1 has as the axle of the joint a slideably arranged bolt 4 for detachably connecting a first bolt-receiving device 5 of joint 1, said device being integrated in an artificial tooth 3 of the partial denture, with a second bolt-receiving device 6. Bolt-receiving device 6 is connected with tooth 2 of the remaining set of teeth by means of a bridge 7, the two bolt-receiving devices being connected with each other in such a way that they can be rotated with respect to each other.

Bolt 4 is displaceably supported in the first bolt-receiving device 5, whereby its path of displacement in the first bolt-receiving device 5 is restricted on one side by a first stop which is provided in the form of a head 8, and on the other side by a second stop in the form of a snap ring 9 arranged on bolt 4. The first bolt-receiving device 5 has a recess 10 associated with head 8, in which recess head 8 is embedded when the bolt is inserted in the second bolt-receiving device 6. At its face side facing head 8 of bolt 4, the second bolt-receiving device has a recess 11 in order to provide space for a snap ring 9, which radially projects from bolt 4.

The first bolt-receiving device 5 is part of a forked head 12 whose fork is formed by the first bolt-receiving device 5 and a tongue 13 arranged parallel to said first bolt-receiving device 5. Tongue 13 has a through-extending bore 15 corresponding to opening 14 of the first bolt-receiving device 5. The end of bolt 4 opposing head 8 is supported in bore 15 when the bolt 4 is in its pushed-in or inserted position.

Forked head 12 has an anchor 16 for anchoring the forked head in artificial teeth 3 of the partial denture and the connection of the artificial teeth 3 among each other. For this purpose, anchor 16 may extend through the total partial denture. So that the second bolt-receiving device 6 may be detached from bolt 4 in spite of the limited spatial conditions in forked head 12, second bolt-receiving device 6 has in its annular wall a slot 22 which is open on one side towards head 8 of bolt 4 and extends parallel to the bolt. The width of slot 22 is dimensioned in such a way that bolt 4, whose free end projects into the fork of forked head 12 even in the extended position, can be guided through slot 22.

In head 8, bolt 4 has a groove 17 extending parallel to its longitudinal central axis. Groove 17 is engaged by a projection 18 arranged on first bolt-receiving device 5 which blocks bolt 4 against rotation about its longitudinal central axis. This is necessary because the outwardly pointing face 19 of head 8 is continually joined on the surface of artificial tooth 3, in which the first bolt-receiving device 5 is integrated, and is not necessarily designed axially symmetrical relative to the longitudinal central axis of the bolt. Thus, a continuous transition from the surface of artificial tooth 3 to the front surface or face 19 is assured only when bolt 4 is in a defined rotational position.

Preferably, joint 1 is inserted in such a way that head 8 of the bolt 4 points towards the inner side of the teeth and the bolt can be pushed in or inserted with the help of the tongue. Pushing bolt 4 out again is possible, for example with the help of a matching mandrel, which is inserted in the wall of artificial tooth 3 through access opening 20 by way of which the face side of bolt 4 opposing head 8 is accessible.

Figure 2:
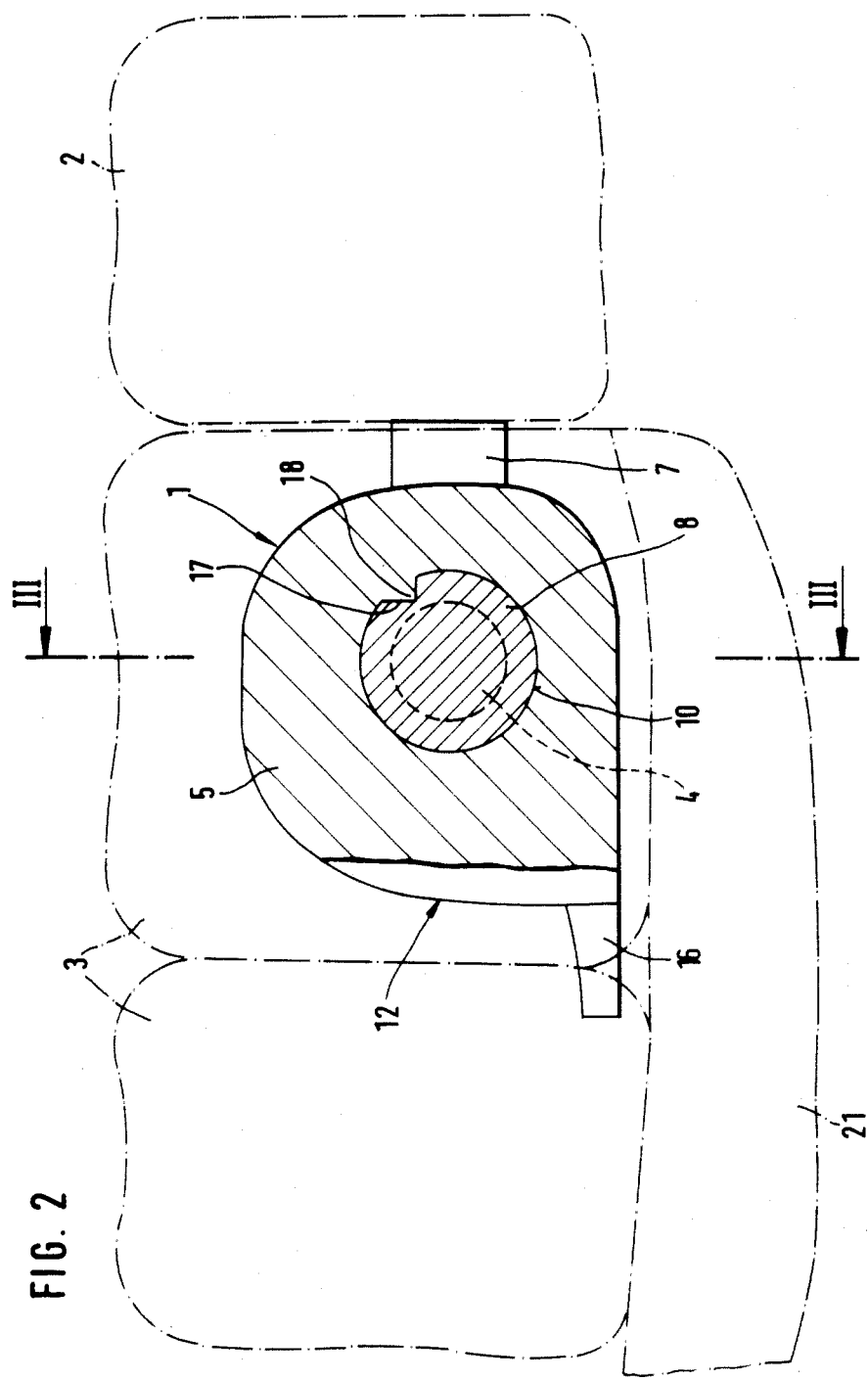
FIG. 2 is a cross-sectional view of the connecting element of the present invention according to FIG. 1 taken along the line II—II of FIG. 1.

In FIG. 2 there is shown a cross-sectional view of the connecting element of the invention taken along the line II—II of FIG. 1. Identical elements of the device are identified by the same reference numerals as in FIG. 1.

As clearly seen in FIG. 2, head 8 of bolt 4 includes groove 17 which is engaged by projection 18 of first bolt-receiving device 5, and artificial teeth 3 of the partial denture have a saddle piece 21 capable of being placed over a crest of the maxilla.

Figure 3:
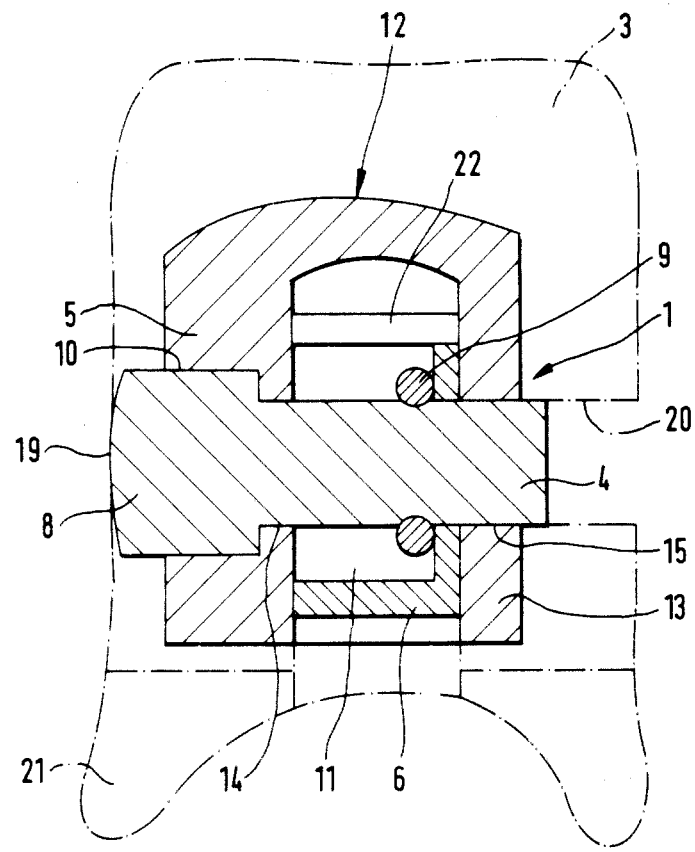
FIG. 3 is a longitudinal cross-sectional view of the connecting element of the present invention taken along line III—III of FIG. 2.

In FIG. 3 there is shown a longitudinal cross-sectional view of the connecting element of the invention taken along the line III—III of FIG. 2. Identical elements of the device are identified by the same reference numerals as in the preceding figures.

FIG. 3 clearly shows the shape of saddle piece 21, which is designed in such a way that it is capable of partly gripping around a crest of the maxilla. Furthermore, FIG. 3 shows a lateral restriction or limitation of slot 22, which slot is disposed in the annular wall of second bolt-receiving device 6. This slot permits second bolt-receiving device 6 to be pulled from the forked head and released by bolt 4 although the bolt continues to project into the intermediate space between first bolt-receiving device 5 and tongue 13 even when in the extended or pulled-out position.

Figure 4:
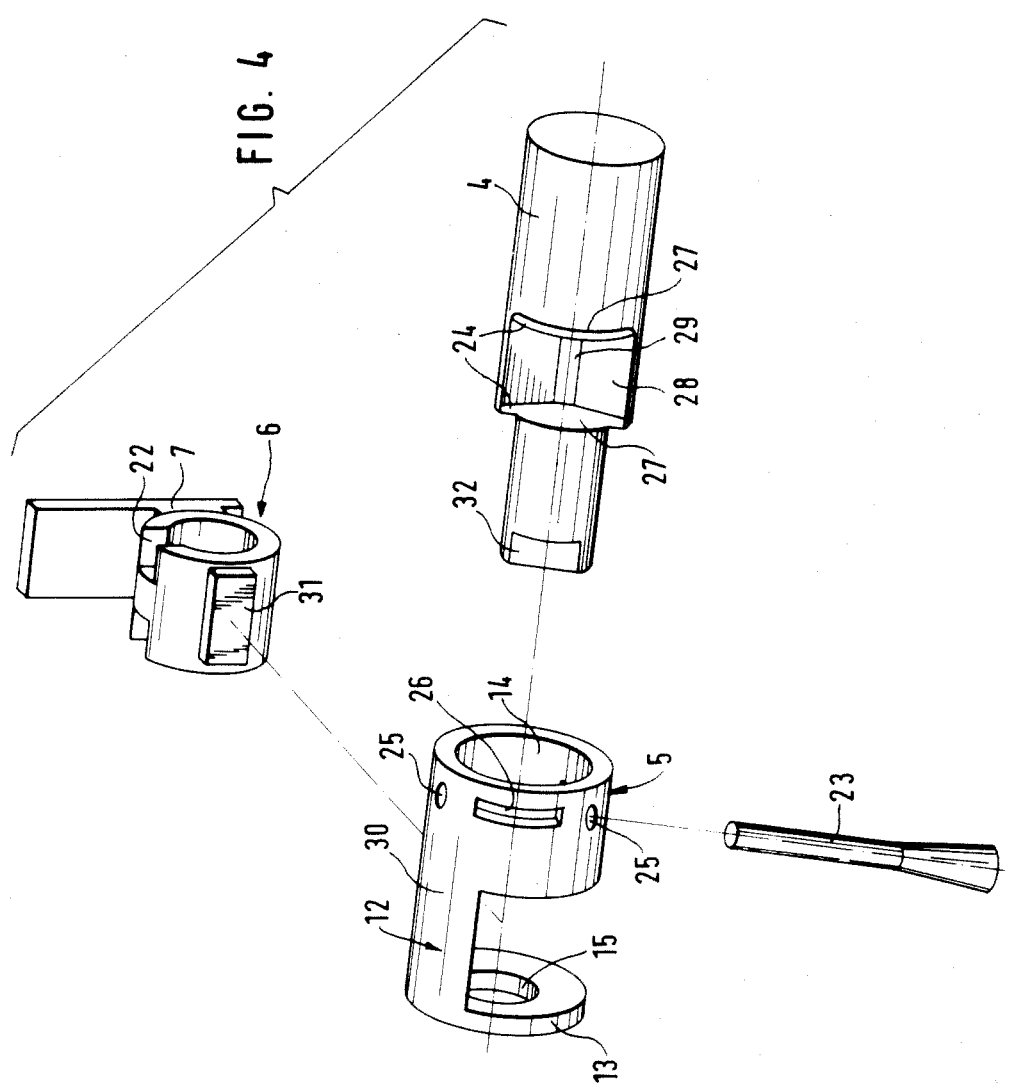
FIG. 4 is an exploded view of a second embodiment of a connecting element according to the present invention.

In FIG. 4 there is shown an exploded view of a second embodiment of a connecting element. Identical elements of the device are identified by the same reference numerals as in the preceding figures.

FIG. 4 clearly shows forked head 12, which is formed by first bolt-receiving device 5 and a tongue 13 aligned parallel to the first bolt-receiving device. The device and tongue are connected with each other by a connecting element 30. Bolt 4 can be inserted in or pushed into forked head 12 through the opening 14 of first bolt-receiving device 5 and the through-extending bore 15 of tongue 13, said bore conforming to said device 5. A pin 23 can be inserted in or pushed into the wall of first bolt-receiving device 5 in a secant-like manner, whereby the ends of the pin are supported in holes 25 which are provided in the wall of the first bolt-receiving device. Bolt 4 is provided with the two receiving elements 24 provided in the form of grooves, which limit the path of displacement of bolt 4 and permit pin 23 to be engaged therein. The flanks of grooves 24 that are closest to the face sides are designed as stops 27 for pin 23 which limit the path of displacement of bolt 4. Area 28 of bolt 4 which is disposed between the receiving elements or grooves 24 and support the pin, is bevelled to form a hip roof-like profile, on whose ridge line 29 pin 23 slidingly rests when bolt 4 is displaced. By said hip roof-like profile, pin 23 is arched or bent in the direction of the wall of the first bolt-receiving device which is provided with a recess 26 for receiving the center portion of arched pin 23.

Second bolt-receiving device 6 can be inserted between the first bolt-receiving device 5 and tongue 13 within the zone of forked head 12. This second bolt-receiving device is hingedly connected with forked head 12 by inserted bolt 4. Second bolt-receiving device 6 has a projection 31 which, when second bolt-receiving device 6 is inserted in the forked head 12, radially projects into the intermediate space between the first bolt-receiving device 5 and the tongue 13. This projection 31 comes to rest against the connecting element 30 of the forked head 12 when the two bolt-receiving devices 5 and 6 are in predetermined rotary positions relative to each other, thereby limiting the angle of rotation of the two bolt-receiving devices 5 and 6 relative to each other.

Even when bolt 4 is extended or pulled out, but still interlocked with pin 23, end 32 of the bolt continues to project into the second bolt-receiving device 6. So that the second bolt-receiving device may be removed from forked head 12 while the bolt is in said position, the second bolt-receiving device has the slot 22 through which the flattened end 32 of the bolt 4 may be extended, or guided.

Figure 5:
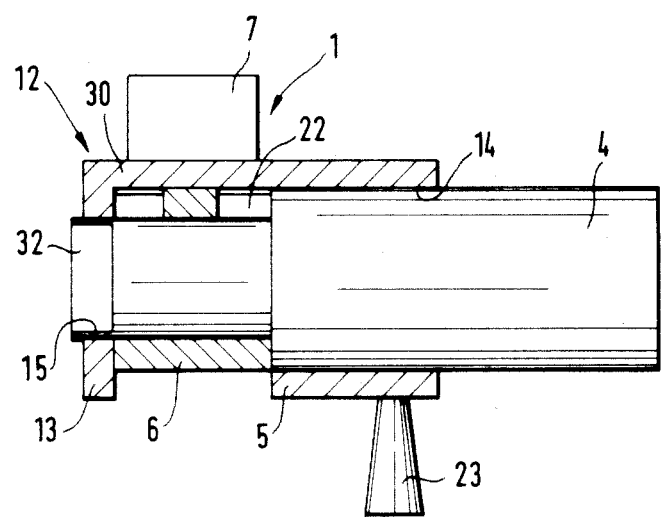
FIG. 5 is a longitudinal cross-sectional view of the connecting element of FIG. 4.

In FIG. 5 there is shown a longitudinal cross-sectional view of the connecting element according to FIG. 4. FIG. 5 clearly shows the connecting element in the assembled state, showing how the individual components of the device cooperate. Identical elements of the device are identified by the same reference numerals as in FIG. 4.

While a few embodiments of the present invention have been shown and described, it will be obvious that many changes and modifications may be made thereunto without departing from the spirit and scope of the invention.

What is claimed is:

1. A connecting element for detachably connecting a partial denture with a remaining set of teeth, comprising:
    a joint having an axle in the form of a bolt displaceably supported in the joint transversely to the row of teeth,
    said joint including two ring shaped bolt receiving devices, a first one of said bolt receiving devices being connectable with the partial denture and a second one of said bolt receiving devices being connectable with the remaining set of teeth, said bolt connecting said first and second bolt receiving devices with each other and being displaceably supported in said first bolt receiving device, and
    a flexible arresting or locking pin projecting into the path of displacement of said bolt and which is arranged on said first bolt receiving device, said arresting pin being engageable in two grooves arranged in said bolt transverse to the longitudinal axis thereof, each wall area of section of said grooves closest to the face sides or said bolt forming a stop limiting the path of displacement of said bolt, the wall of said first bolt receiving device having two aligned holes for receiving the ends of said arresting pin and an oblong recess arranged in the wall between said holes for receiving said pin and extending parallel to said pin.

2. The connecting element of claim 1, wherein said first bolt-receiving device forms part of a forked head whose fork is formed by said first bolt-receiving device and a tongue arranged approximately parallel to said first bolt-receiving device, said tongue having a through-extending bore conforming to the opening of the ring-shaped first bolt-receiving device, the diameter of said bore conforming to the diameter of said bolt, and the minimum spacing between said first bolt-receiving device and said tongue conforming to the width of said second bolt-receiving device.

3. The connecting element of claim 2, wherein said second bolt-receiving device has an outwardly protruding projection, said projection striking a connecting element of said forked head when said second bolt-receiving device is inserted in said forked head with the bolt-receiving devices in a predetermined rotary position relative to each other, said connecting element connecting said first bolt-receiving device and said tongue to each other to form said fork.

4. The connecting element of claim 2, wherein said second bolt-receiving device has a slot disposed in its annular wall open on one side towards the face side of said second bolt-receiving device facing said first bolt-receiving device, and said slot has a minimum width conforming to the thickness of the end of said bolt projecting into said second bolt-receiving device when the bolt is in the pulled-out position.

5. The connecting element of claim 4, wherein the end of said bolt projecting into said second bolt-receiving device is laterally flattened.

6. The connecting element of claim 1, characterized by the fact that said recess is a slot.

7. The connecting element of claim 1, wherein the area of said bolt supporting said pin and being limited by said grooves is bevelled to form an approximately hip roof-like profile whose ridge line extending parallel to the longitudinal axis of the bolt slidingly rests against said pin.

* * * * *